US00PP11385P

United States Patent [19]

Toyama

[11] Patent Number: Plant 11,385

[45] Date of Patent: May 16, 2000

[54] CHERRY TREE NAMED 'PC 7144-6'

[75] Inventor: Thomas K. Toyama, Eugene, Oreg.

[73] Assignee: Washington State University Research Foundation, Pullman, Wash.

[21] Appl. No.: 09/066,066

[22] Filed: Apr. 24, 1998

[51] Int. Cl.[7] ..... A01H 5/00

[52] U.S. Cl. ..... Plt./181

[58] Field of Search ..... Plt./181

[56] References Cited

U.S. PATENT DOCUMENTS

P.P. 8,051 12/1992 Toyama ..... Plt./181

P.P. 10,459 6/1998 Toyama ..... Plt./181

*Primary Examiner*—Howard J. Locker
*Assistant Examiner*—Wendy A Baker
*Attorney, Agent, or Firm*—Chernoff, Vilhauer, McClung & Stenzel

[57] ABSTRACT

A new and distinct variety of self-infertile sweet cherry tree which bears very large mahogany red colored fruits that are 10–14 grams in weight. Its fruits, which are well suited for the high quality early season premium market, ripen six to nine days ahead of the commercially grown 'Bing' variety, to which in many ways the new variety is comparable.

4 Drawing Sheets

BACKGROUND AND SUMMARY OF THE INVENTION

The present invention relates to a new variety of sweet cherry tree (*Prunus avium*) which bears very large, firm, attractive fruits of excellent quality and flavor. 'PC 7144-6' was developed at the Washington State University's Irrigated Agriculture Research and Extension Center (I.A.R.E.C.) at Prosser, Wash. It was selected from among several seedlings of the variety 'Stella' (unpatented variety)×'Early Burlat' (unpatented variety) from crossed made in 1971 and has continued to be tested as 'PC 7144-6'. The new variety will be marketed under the trademarked name TIETON. Second tests trees were planted on the Roza Unit of the center in the spring of 1978 and came into production in 1982.

Fruit of the 'PC 7144-6' is a very large, dark red, high quality, mild flavored cherry similar to 'Bing' (popular unpatented commercial variety) having larger fruit that ripens six to nine days ahead of 'Bing'. It is self-infertile with a slightly early bloom period that overlaps that of 'Bing'. Its rain-cracking susceptibility and chilling requirement are similar to that of 'Bing'. The extraordinary size (10 to 14 grams, 28 to 32 millimeters in width) of 'PC 7144-6' fruit, with export-quality firmness and early ripening date, make it a cherry with very high potential for premium markets.

The subject variety resembles 'Bing' in shape and appearance but is noticeably larger in size. The trees have been only moderately productive, producing flowers in clusters of no more than three to four, resulting some years in light crops.

Fruit stems are short to medium length when compared to those of 'Bing'. Fruit shape is broadly cordate and the flesh, which colors slowly, is light to medium red.

Fruit buds of 'PC 7144-6' have winter hardiness comparable to those of Bing as demonstrated by winter freezes at the test site near Prosser in December 1990 and February 1996.

The tree is vigorous and spreading in shape and has proven to be an annual bearer of large firm fruits.

Soluble solids are slightly less than 'Bing' when comparing fruits of equal maturity. The seeds are semi-freestone and large. All second and third generation test trees observed closely have shown no tendency toward the "cherry crinkle-leaf" genetic disorder which is common in 'Bing', as well as in several other varieties of sweet cherry.

Interest in this new variety is for its firm, early, high quality shipable fruit for the early season premium market.

Trees of the subject variety are vigorous and following several years of testing have proven compatible with all common rootstocks used under sweet cherry trees.

Asexual reproduction of this new and distinct variety shows that its desirable characteristics come true to form and are established and transmitted through succeeding propagation's by grafting at our test facilities near Prosser.

BRIEF DESCRIPTION OF THE DRAWINGS

In the accompanying drawings vegetative growth, fruit and seeds are shown in color as nearly true as is reasonably possible to make in color photographs of this nature.

DESCRIPTION OF THE INVENTION

Figure 1:
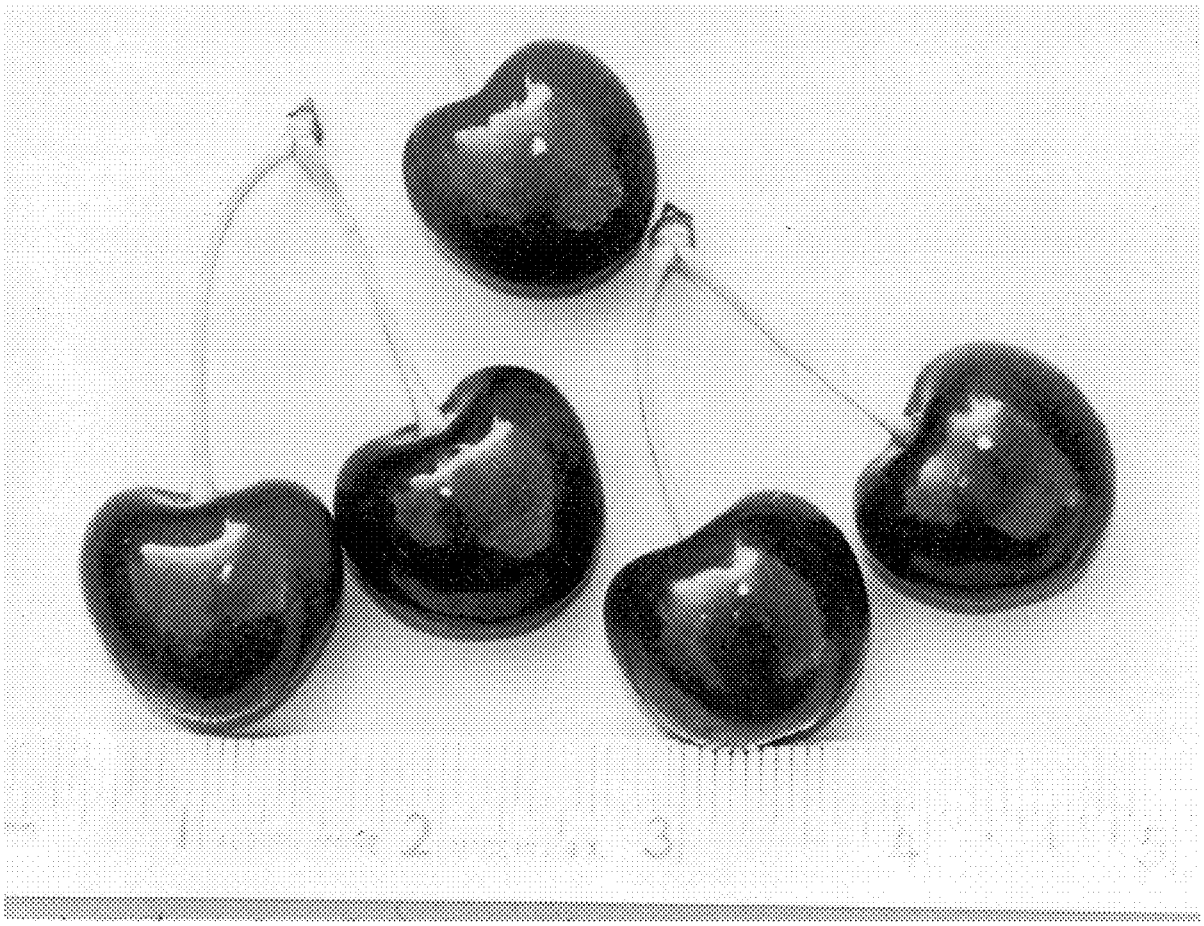
FIG. 1 shows fruit of the subject variety, demonstrating large size and shape of fruits and short-to-medium stem length.
Figure 2:
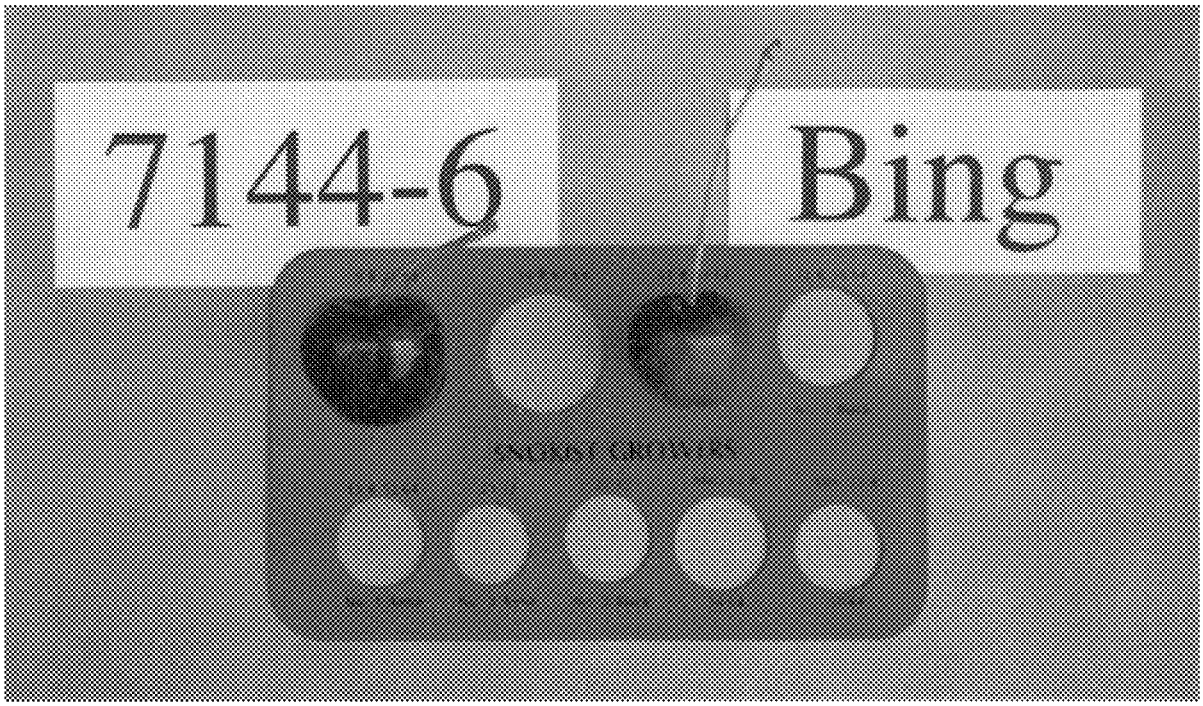
FIG. 2 compares size and shape of mature 'PC 7144-6' and 'Bing' fruits.
Figure 3:
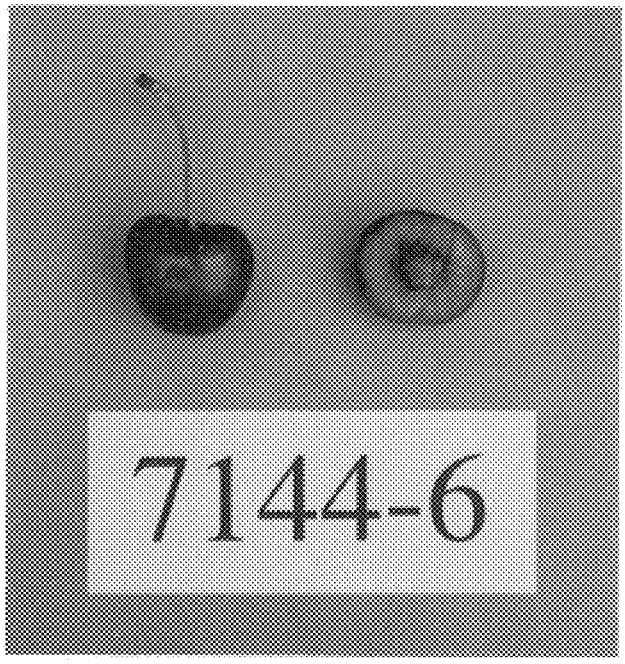
FIG. 3 shows 'PC 7144-6' fruits with a seed exposed and light red flesh color.
Figure 4:
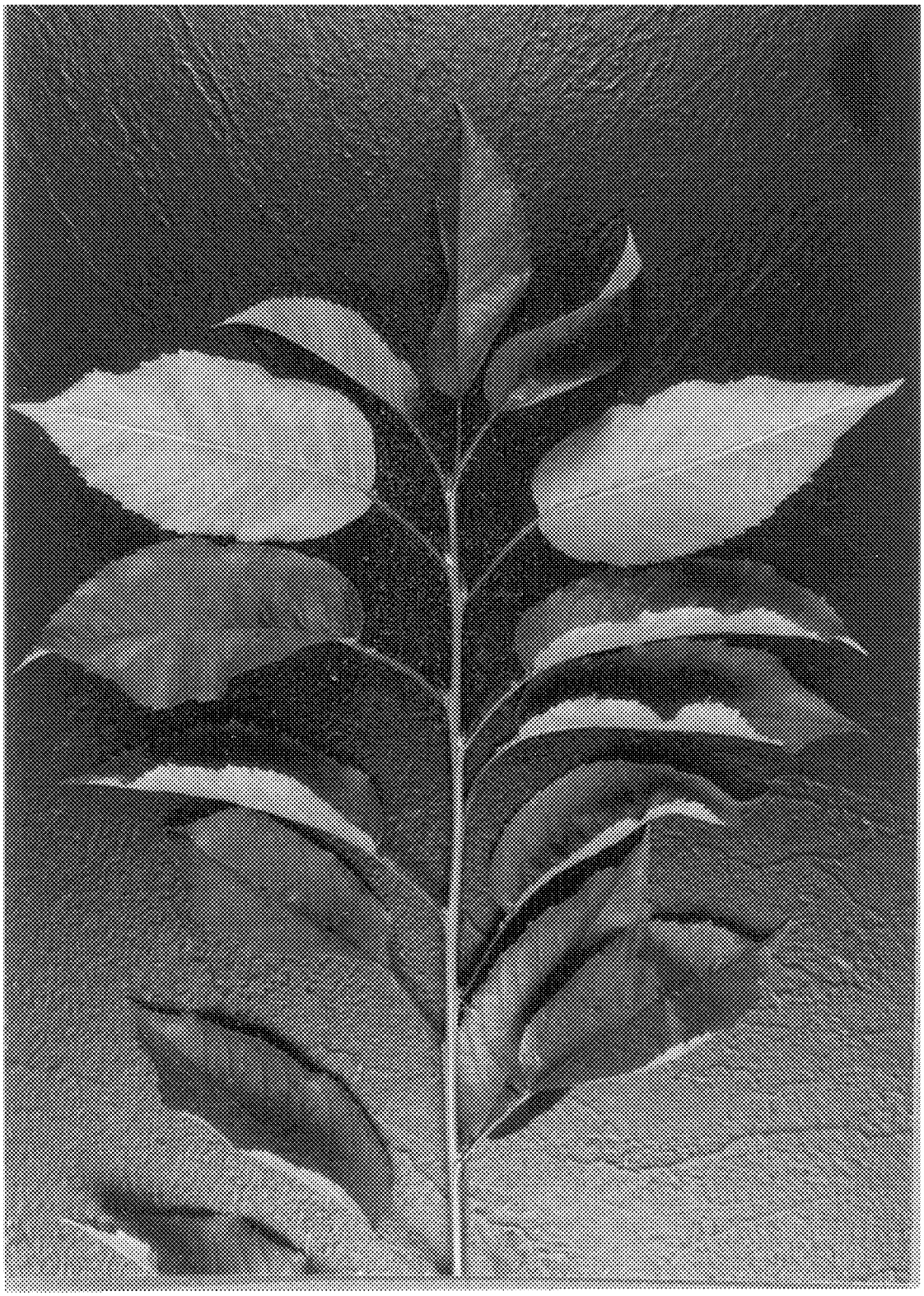
FIG. 4 shows a branch and leaves of the subject variety.
Figure 5:
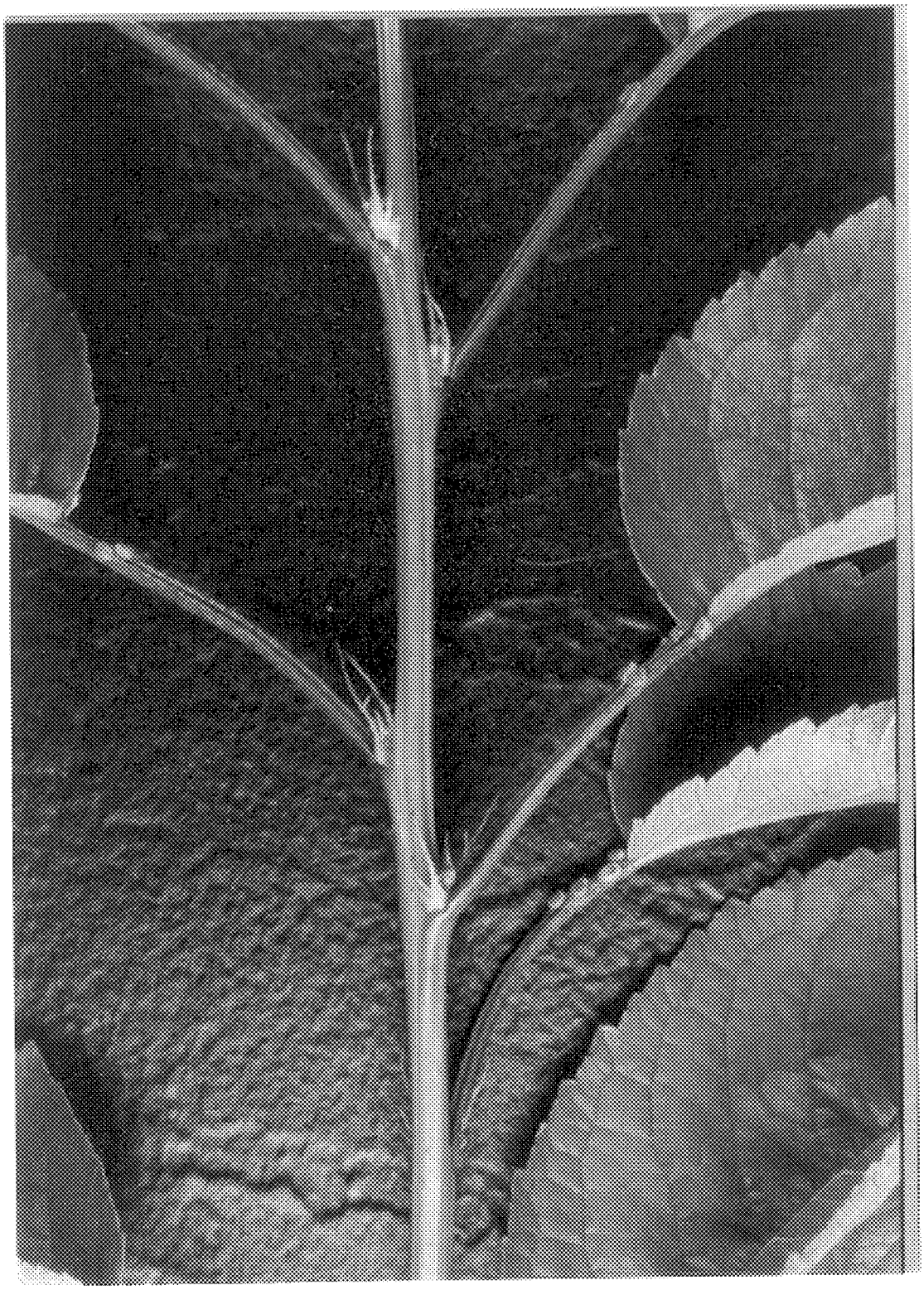
FIG. 5 shows a branch of current season's growth of the subject variety.

Following is a detailed description of the new variety of cherry tree with color terminology in accordance with the Munsell Color Cascade chart except where general color terms of ordinary dictionary significance are used.

Tree:

*Size.*—Large: average size of 6-year-old trees of 'Mazzard' seedling rootstocks is 16 feet high and 16 feet wide.

*Vigor.*—Vigorous: average growth of 6-year-old trees is 26 inches per year.

*Branching habit.*—Upright-spreading.
*Density.*—Average for sweet cherry.
*Form.*—Round-headed when mature.
*Hardiness.*—Hardy in area where tested (lower Yakima Valley of Washington).
*Production.*—Moderately productive: average 15.6 lbs/5-year-old tree in 1998 and 19.8 lbs/6-year-old tree in 1999.
*Bearing.*—Consistent, regular.
*Trunk.*—Size: Stocky. Bark Texture: Typical for sweet cherry. Bark color: Grey-brown (26-13). Lenticels: Numerous; medium 3.1–5.2 mm in diameter; brown.
*Branch.*—Size: Stocky. Crotch angle of bearing branches: 60–75° from vertical. Texture: Average, typical for sweet cherry. Color: First year wood, light green (24-1); second year wood, brownish green (24-13). Lenticels: Numerous; small, 1.5–2.0 mm in diameter; brown.
*Leaves.*—Measurements are from mature leaves attached at midpoint of actively growing upright shoots of current-season's growth. Size: Very large: 18–19 cm long, 7–8 cm wide. Form: Lanceolate with acuminate tip. Color: Upper surface glossy green (20-13), lower surface light green (22-9). Midvein: Large; red (40-7), 1.5 mm in diameter. Petiole: Medium to short; 2.5 to 3 cm long, 3 mm thick; red on upper side, light pink on under side, darker red tinge along petiole groove. Texture: Smooth. Margin: Crenate to finely serrate. Glands: Variable in number (2–4); compressed; positioned both alternate and irregular; large, oval to reniform shape; shiny with slightly reddish, indented center when immature; darker red (38-13) when mature; glabrous; positioned on rim of petiole groove starting 3–4 mm from base of leaf petiole. Stipules: Medium; usually two 1.5–2.0 cm in length; pink (41-2).

Flower buds:
*Hardiness.*—Hardy.
*Size.*—Medium to large.
*Length.*—Medium.
*Form.*—Very plump, conic, free.

Flowers: Self-infertile, both 'Bing' and 'Lapins' (unpatented) are compatible pollinators.
*First bloom.*—April 5 at Prosser test site (10-year average), early when compared with other varieties.
*Full bloom.*—April 11 at Prosser test site.
*Size.*—Large, 25–30 mm in diameter when fully open.
*Color.*—White.
*Bloom count.*—Few, usually 3–4 per cluster.
*Petals.*—Large, 19–20 mm in length and 15–16 mm in width; obovate, cupped slightly inward; white.
*Nectaries.*—Light green when mature (22-7).
*Anthers.*—Large, yellow (27-4).
*Pollen.*—Abundant, yellow (27-6).
*Pedicel.*—Medium length 13–14 mm, light green (23-6).

Fruit:
*Maturity.*—Eating ripe June 9 at Prosser test site (10-year average).
*Date of first picking.*—June 9 at Prosser.
*Date of last picking.*—June 16 at Prosser.
*Size.*—Very large 10–14 grams; diameter transversely across suture 3–3.4 cm; diameter apically 2.8–3 cm.
*Form.*—Uniform, symmetrical, broadly cordate, slightly flattened apex end.
*Suture.*—Very shallow, very slight darker mahogany colored line extends from base to apex.
*Base.*—Rounded.
*Apex.*—Slightly flattened, distinctive medium-to-large white dot.
*Stem.*—Thick, short, 2.5–3 cm in length; light green (21-8).
*Skin.*—Thickness: Medium. Texture: Medium. Tenacity: Tenacious to flesh. Tendency to crack: Susceptible to cracking caused by prolonged rains about the same as 'Bing'; none in dry season. Down: Wanting. Color: Mahogany red (41-15).
*Flesh.*—Color: Light red (41-13). Surface of pit cavity: Red (39-15). Texture: Very firm, crisp. Fibers: Few, cream color, fine. Ripens: Evenly. Flavor: Sweet, low acid. Juice: Light red (38-8). Aroma: Slight. Eating quality: Very good.
*Stone.*—Type: Semi-free. Size: Large, 1.5 cm long, 1.2 cm wide. Form: Oval with small protruding wing along basal shoulder of ventral suture. Base: Rounded. Helium: Oval to slightly oblong. Apex: Rounded. Sides: Equal. Surface: Smooth. Ventral edge: Narrow suture subtended by two low ridges converging basally and apically. Dorsal edge: Broad; smooth, narrow ridge from base to apex. Color: Light brown (29-9) when dry. Tendency to split: None.

Use: Early season shipping to premium fresh markets.
Keeping quality: Good.
Resistance to insects and diseases: Susceptible to bacterial canker (*pseudomonas*), no cherry crinkle-leaf noted.
Shipping quality: Firm, excellent, at least as good as 'Bing'.
Variance in botanical details: The cherry tree and its fruit herein described will vary due to climate, soil and growing conditions under which it may be grown. The present description being of the variety as grown in the Lower Yakima Valley of Washington. Comparisons to the 'Bing' variety are referenced to 'Bing' cherry trees growing in the same area under similar circumstances.

I claim:

1. A new and distinct variety of cherry tree obtained as a seedling of 'Stella' (unpatented)×'Early Burlat' (unpatented), substantially as shown and described herein, characterized by its early maturing, very large, firm fruits that are larger than the fruits of the 'Bing' variety and ripen six to nine days earlier, and by its resistance to crinkle-leaf disorder.

* * * * *